(12) United States Patent
Sasaki

(10) Patent No.: US 8,449,759 B2
(45) Date of Patent: *May 28, 2013

(54) APPARATUS AND METHOD FOR CONTROLLING A GAS SENSOR

(75) Inventor: Hisashi Sasaki, Kohnan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 60 days.

This patent is subject to a terminal disclaimer.

(21) Appl. No.: 13/004,345

(22) Filed: Jan. 11, 2011

(65) Prior Publication Data

US 2011/0168573 A1    Jul. 14, 2011

(30) Foreign Application Priority Data

Jan. 14, 2010 (JP) ................................. 2010-005606

(51) Int. Cl.
*G01N 27/407* (2006.01)

(52) U.S. Cl.
USPC .......... 205/781; 204/424; 73/23.32; 701/103; 702/24

(58) Field of Classification Search
USPC ...... 204/410, 411, 421–429, 781, 783.5–785, 204/787; 205/781, 783.5–785, 787; 123/672–703; 73/23.31, 23.32; 60/274–293; 701/103; 702/24

See application file for complete search history.

(56) References Cited

U.S. PATENT DOCUMENTS

| | | | |
|---|---|---|---|
| 5,752,491 A * | 5/1998 | Schmitz et al. | 123/672 |
| 5,762,055 A * | 6/1998 | Yamashita et al. | 123/677 |
| 6,099,717 A * | 8/2000 | Yamada et al. | 205/784.5 |
| 6,214,207 B1 | 4/2001 | Miyata et al. | |
| 6,347,544 B1 | 2/2002 | Hada et al. | |
| 6,868,712 B2 | 3/2005 | Hada et al. | |
| 2002/0162743 A1* | 11/2002 | Inagaki | 204/425 |
| 2004/0047396 A1* | 3/2004 | Nomura et al. | 374/141 |
| 2004/0238378 A1* | 12/2004 | Kumazawa et al. | 205/781 |
| 2007/0119709 A1 | 5/2007 | Oya et al. | |
| 2009/0051373 A1 | 2/2009 | Kato et al. | |
| 2009/0229343 A1* | 9/2009 | Ishiguro et al. | 73/23.31 |
| 2011/0168574 A1* | 7/2011 | Sasaki | 205/775 |

FOREIGN PATENT DOCUMENTS

| | | |
|---|---|---|
| EP | 0887640 A1 | 12/1998 |
| JP | 10-142194 A | 5/1998 |
| JP | 2002-303601 A | 10/2002 |
| JP | 2007-101485 A | 4/2007 |

* cited by examiner

*Primary Examiner* — J. Christopher Ball
*Assistant Examiner* — Jennifer Dieterle
(74) *Attorney, Agent, or Firm* — Sughrue Mion, PLLC

(57) ABSTRACT

A gas sensor control apparatus including internal resistance detection means for detecting an internal resistance value of one of cells of a gas sensor, concentration detection means for detecting a concentration value of a specific gas component in a gas to be measured and outputting the detected concentration value, heater current supply control means for controlling a current to be supplied to a heater of the gas sensor such that the detected internal resistance value becomes a target value, determination means for determining whether or not the detected internal resistance value is within a permissible range including the target value, nullification information generation means for generating nullification information to nullify the detected concentration value, when it is determined that the target value is out of the permissible range, and nullification information output means for outputting the nullification information to an external device connected to the gas sensor control apparatus.

3 Claims, 7 Drawing Sheets

APPARATUS AND METHOD FOR CONTROLLING A GAS SENSOR

BACKGROUND OF THE INVENTION

The present invention relates to a gas sensor control apparatus adapted for connecting to a gas sensor which includes at least one cell having a solid electrolyte layer and a pair of electrodes, and a heater, detecting a concentration of a specific gas component in a gas to be measured via the gas sensor, outputting the concentration detected to an outside thereof and controlling supply of an electric current to the heater, and relates to a method for controlling the gas sensor.

An oxygen sensor and an air-fuel ratio sensor are known as a gas sensor which is used for enhancing fuel economy and controlling combustion in an internal combustion engine for a vehicle such as an automobile. In addition, with enforcement of strict automobile emission control, there is a demand for reduction of nitrogen oxide (NOx) in exhaust gas. To meet the demand, a NOx sensor capable of directly detecting a NOx concentration has been proposed.

As such a gas sensor, there are known those sensors which include a plurality of cells each having an oxygen ion-conducting solid electrolyte (for instance, zirconia) body and a pair of electrodes formed thereon. Particularly, as a NOx sensor having the above structure, there is known a NOx sensor in which a first oxygen pumping cell and a second oxygen pumping cell are laminated. In this NOx sensor, a first measurement chamber into which a gas to be measured is introduced is defined and the first oxygen pumping cell exposed to the first measurement chamber controls an oxygen concentration in the gas at a constant value. The gas having the thus controlled oxygen concentration flows into a second measurement chamber communicated with the first measurement chamber. A constant electric voltage is applied to the second oxygen pumping cell exposed to the second measurement chamber to thereby decompose the NOx present in the gas in the second measurement chamber. As a result, an electric current corresponding to the NOx concentration flows through the second oxygen pumping cell, so that the NOx concentration is detected on the basis of the electric current.

For the purpose of performing accurate detection of the NOx concentration, it is necessary to activate each of cells by heating the NOx sensor to a predetermined activation temperature (for instance, 750° C. or higher). Therefore, the NOx sensor is provided with a unitary body constituted of a heater and each of cells and is connected to a controller which controls an electric current to be supplied to the heater. Such a NOx sensor control apparatus is disclosed in Japanese Patent Application Unexamined Publication No. 10-142194. The NOx sensor control apparatus of this conventional art measures an internal resistance (impedance) of one of cells constituting a NOx sensor, calculates a temperature of the NOx sensor (an element temperature) on the basis of the measured internal resistance and controls supply of an electric current to a heater such that the temperature calculated becomes equal to a target temperature. In addition to such a control function of supplying the current to the heater, the NOx sensor control apparatus ordinarily has functions of converting the current flowing in the second oxygen pumping cell to voltage, calculating a detection value of the NOx concentration (a NOx concentration conversion value) on the basis of the converted voltage, and outputting the detection value to an external engine control unit.

On the other hand, in such a gas sensor control apparatus, there will occur such a problem that the output detection value of the internal resistance of the cell is considerably different from an actual internal resistance value due to noise superimposed on a signal of the output detection value. In order to solve this problem, a technology of controlling a gas sensor is disclosed in Japanese Patent Application Unexamined Publication No. 2002-303601. In this conventional art, variation in amount of the internal resistance to be detected by the gas sensor control apparatus is limited to thereby reduce influence of noise and perform accurate control of the gas sensor.

SUMMARY OF THE INVENTION

However, a gas sensor such as a NOx sensor is mounted to an exhaust pipe or the like of a vehicle, thereby allowing the gas sensor to undergo rapid change of an ambient temperature of the gas to be measured surrounding the gas sensor (i.e., an exhaust gas flowing through the exhaust pipe). As a result, there will occur cooling (so-called element cooling) or rapid temperature rise in the gas sensor (the gas sensor element including at least one cell and a heater). Further, if the internal resistance value of the cell is temporally largely changed due to the element cooling or the rapid temperature rise, the detection value of the gas concentration (the NOx concentration or the like) will be changed to thereby cause deterioration of accuracy in detecting concentration of specific gas components in the gas to be measured.

The present invention has been made in view of the above problems. It is an object of the present invention to provide an apparatus and method for controlling a gas sensor which is capable of suppressing deterioration of accuracy in detecting a concentration of specific gas components in a gas to be measured even when an internal resistance value of a cell is changed due to element cooling or the like.

In a first aspect of the present invention, there is provided a gas sensor control apparatus adapted for connecting to a gas sensor including a plurality of cells which each include a solid electrolyte layer and a pair of electrodes disposed on the solid electrolyte layer, and a heater adapted for heating at least one of the cells. The gas sensor is adapted for outputting a concentration signal corresponding to a concentration of a specific gas component present in a gas to be measured via one of the cells. The gas sensor control apparatus is adapted for connecting with an external device and includes:

internal resistance detection means for detecting a value of an internal resistance of one of the cells as an objective cell;

concentration detection means for detecting a value of the concentration of the specific gas component on the basis of the concentration signal and outputting the value of the concentration;

heater current supply control means for controlling a current to be supplied to the heater such that the value of the internal resistance detected by the internal resistance detection means becomes a target value;

determination means for determining whether or not the value of the internal resistance detected by the internal resistance detection means is within a permissible range including the target value;

nullification information generation means for generating nullification information to nullify the value of the concentration detected by the concentration detection means, when it is determined by the determination means that the target value is out of the permissible range; and nullification information output means for outputting the nullification information to the external device.

In the gas sensor control apparatus according to the first aspect of the present invention, when a value of the internal resistance of an objective cell which is detected by the gas sensor control apparatus is out of the permissible range, nullification information for nullifying the detected value of the concentration is transmitted to the external device. As a result, the external device connected to the gas sensor control apparatus can perform appropriate processing such as processing for nullifying the value of the concentration separately obtained, on the basis of the nullification information. Accordingly, even in a case where variation in the value of the concentration of the specific gas component becomes larger as the internal resistance of the gas sensor is rapidly changed due to element cooling or the like, the nullification information for nullifying the detected value of the concentration is transmitted to the external device together with the detected value of the concentration to thereby suppress deterioration in accuracy in detecting the concentration of the specific gas component.

In a second aspect of the present invention, there is provided the gas sensor control apparatus according to the first aspect, wherein the gas sensor is a NOx sensor including a first measurement chamber defined between adjacent two of the solid electrolyte layers which are laminated spaced apart from each other, the gas to be measured being introduced from an outside into the first measurement chamber, and a second measurement chamber communicated with the first measurement chamber and defined by surrounding portions in the NOx sensor, the cells including:

an oxygen concentration measurement cell including a detection electrode disposed to be exposed to an inside of the first measurement chamber, and a reference electrode which is a counter electrode relative to the detection electrode, the oxygen concentration measurement cell outputting an output voltage corresponding to an oxygen concentration in the first measurement chamber, a first pumping cell including an inside first pump electrode disposed to be exposed to an inside of the first measurement chamber and a first counter electrode which is a counter electrode relative to the inside first pump electrode and disposed on an outside of the first measurement chamber, the first pumping cell controlling the oxygen concentration in the first measurement chamber by controlling a current flowing between the inside first pump electrode and the first counter electrode such that the output voltage from the oxygen concentration measurement cell becomes a predetermined value, and a second pumping cell including an inside second pump electrode disposed to be exposed to an inside of the second measurement chamber into which a gas whose oxygen concentration is controlled by the first pumping cell is introduced from the first measurement chamber, and a second counter electrode which is a counter electrode relative to the inside second pump electrode and disposed on an outside of the second measurement chamber, the second pumping cell through which a current corresponding to a concentration of NOx as the specific gas component present in the gas introduced into the second measurement chamber is flowed by applying a voltage between the inside second pump electrode and the second counter electrode, wherein one of the oxygen concentration measurement cell, the first pumping cell and the second pumping cell is the objective cell.

In such a NOx sensor, a value of the current corresponding to the NOx concentration which flows through the second pumping cell is considerably small such as nA and µA order. Therefore, when there occurs a rapid change in the internal resistance due to element cooling or the like, a large variation in the value of the current is caused. In a case where the gas sensor control apparatus according to the present invention is applied to the gas sensor having the above construction, the nullification information is outputted together with the detected value of the concentration even when there occurs a rapid change in the internal resistance due to element cooling or the like. As a result, deterioration in accuracy in detecting the NOx concentration can be effectively suppressed.

In a third aspect of the present invention, there is provided a method of controlling a gas sensor including a plurality of cells which each include a solid electrolyte layer and a pair of electrodes disposed on the solid electrolyte layer, and a heater adapted for heating at least one of the cells. The gas sensor is adapted for outputting a concentration signal corresponding to a concentration of a specific gas component present in a gas to be measured via one of the cells. The gas sensor is adapted for connecting to a gas sensor control apparatus which is connected with an external device. The method includes:

an internal resistance detection step of detecting a value of an internal resistance of one of the cells as an objective cell;

a concentration value detection step of detecting a value of the concentration of the specific gas component on the basis of the concentration signal and outputting the value of the concentration to the external device;

a heater current supply control step of controlling a current to be supplied to the heater such that the value of the internal resistance detected in the internal resistance detection step becomes a target value;

a determination step of determining whether or not the value of the internal resistance detected in the internal resistance detection step is within a permissible range including the target value;

a nullification information generation step of generating nullification information to nullify the value of the concentration which is detected in the concentration value detection step when it is determined in the determination step that the target value is out of the permissible range; and a nullification information output step of outputting the nullification information to the external device.

According to the present invention, even in a case where there occurs variation in value of an internal resistance of a cell of a gas sensor due to element cooling or the like, it is possible to suppress deterioration in accuracy in detecting a concentration of a specific gas component present in a gas to be measured.

DETAILED DESCRIPTION OF THE INVENTION

Figure 1:
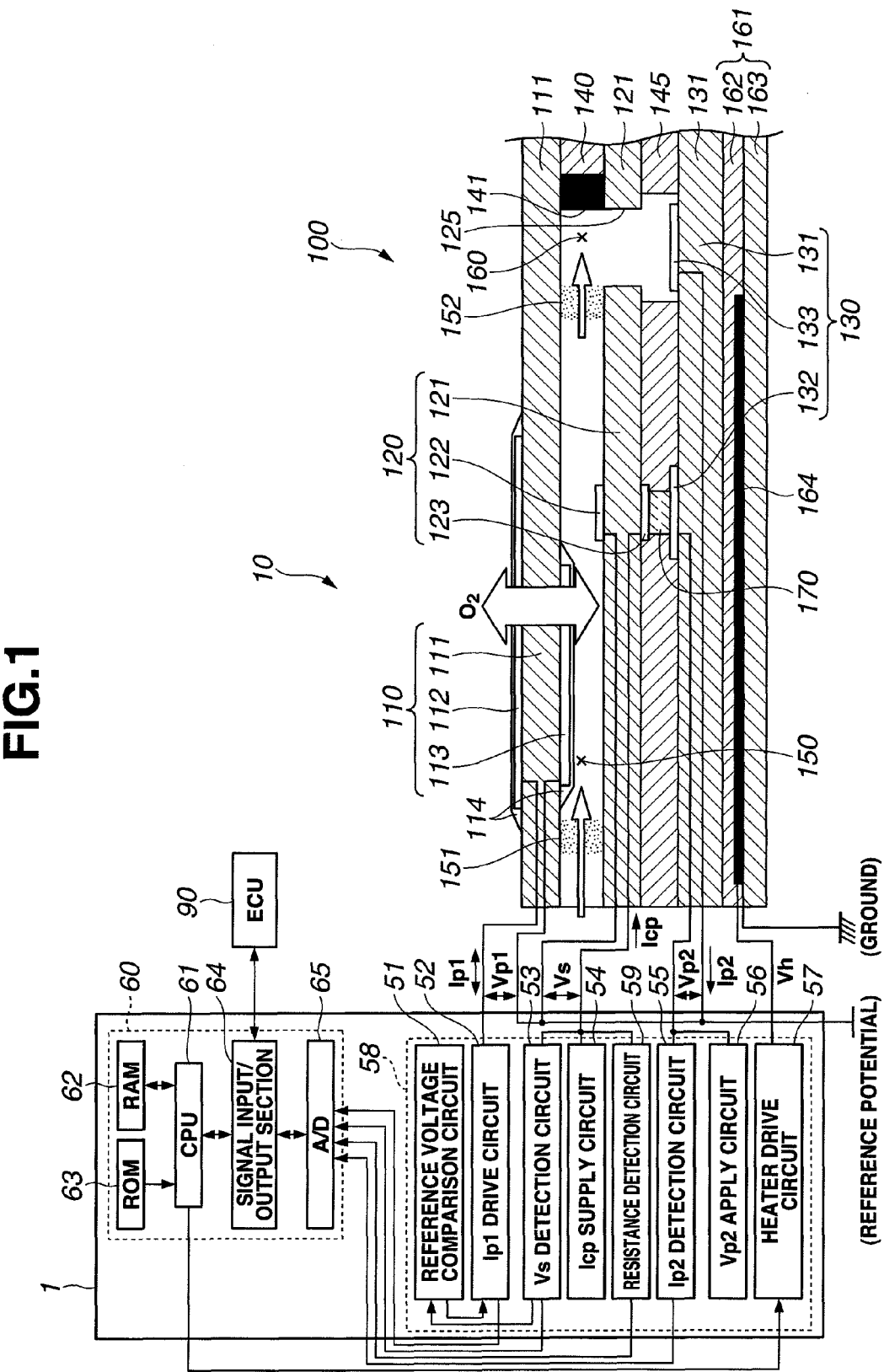
FIG. 1 is a diagram showing a construction of a gas sensor control apparatus according to an embodiment of the present invention and a construction of a gas sensor connected to the gas sensor control apparatus.

In the following, an embodiment of the present invention is explained by referring to the accompanying drawings. FIG. 1 shows a block diagram of a gas sensor control apparatus (controller) 1 according to the embodiment and a structural diagram of a gas sensor 10 connected to the gas sensor control apparatus. The gas sensor control apparatus 1 is installed onto a vehicle equipped with an internal combustion engine (hereinafter also referred to as an engine), not shown. The gas sensor control apparatus 1 is electrically connected to not only a connector (not shown) of the gas sensor (NOx sensor) 10 but also a vehicle-side control apparatus (ECU 90) via a harness. In this embodiment, the gas sensor 10 is a NOx sensor and the gas sensor control apparatus 1 serves as a NOx sensor control apparatus. Therefore, the gas sensor 10 is hereinafter also referred to as the NOx sensor 10 and the gas sensor control apparatus 1 is hereinafter also referred to as the NOx sensor control apparatus 1. The ECU 90 corresponds to an external device in the present invention.

The NOx sensor control apparatus 1 is adapted for calculating a detection value of a NOx concentration (a NOx concentration conversion value) on the basis of a signal outputted from the NOx sensor 10, and outputting the detection value to the ECU 90. The ECU 90 executes processing for controlling an operating condition of the engine in accordance with the detection value of the NOx concentration, as well as processing for purifying the NOx accumulated in a catalyst or processing for detecting an abnormal state of the catalyst. The detection value of the NOx concentration (the NOx concentration conversion value) corresponds to a value of specific gas component concentration in the present invention.

First, the structure of the NOx sensor 10 will be explained. The NOx sensor 10 includes a sensor element 100. FIG. 1 shows an inside structure of a front end portion of the sensor element 100 in a sectional view, which is located on the side of the NOx sensor control apparatus 1.

The sensor element 100 has a narrow elongated plate shape and held in a housing (not shown) which is adapted to be attached to an exhaust pipe (not shown) of the engine. A signal wire for retrieving a signal outputted from the sensor element 100 is derived out of the NOx sensor 10 and electrically connected to the gas sensor control apparatus 1 which is mounted in a position apart from the NOx sensor 10.

The sensor element 100 has a multi-layered laminate structure including three plate-shaped solid electrolyte layers 111, 121, 131 between which insulators 140, 145 made of alumina or the like are sandwiched, respectively. A heater element 161 is disposed on an outside of the solid electrolyte layer 131 (that is, on an opposite side of the solid electrolyte layer 121 as shown in FIG. 1). The heater element 161 includes sheet-like insulating layers 162, 163 which are made of an alumina-based material and stacked on the side of the solid electrolyte layer 131, and a heater pattern 164 which is a Pt-based material and disposed between the insulating layers 162, 163 in an embedded state. The heater element 161 acts to generate heat when a current (electric current) is supplied to the heater pattern 164. The heater element 161 corresponds to a heater in the present invention.

The solid electrolyte layers 111, 121, 131 are made of zirconia and have oxygen ion conductive property.

Porous electrodes 112, 113 are disposed on both opposite surfaces of the solid electrolyte layer 111 in a direction of lamination of respective layers of the sensor element 100 so as to sandwich the solid electrolyte layer 111 therebetween. The electrodes 112, 113 are made of Pt or Pt alloy, cermet containing Pt and ceramic, or the like. A porous protective layer 114 is disposed on an outer surface of the respective electrodes 112, 113 and protects the electrodes 112, 113 from being exposed to poisoning gas (reducing atmosphere) present in exhaust gas and being deteriorated by the poisoning gas.

By flowing a current between the electrode 112 and the electrode 113, pumping-out and pumping-in of oxygen (so-called oxygen pumping) can be carried out between the atmosphere contacted with the electrode 112 (the atmosphere on an outside of the sensor element 100) and the atmosphere contacted with the electrode 113 (the atmosphere on an inside of a first measurement chamber 150 as explained later) via the solid electrolyte layer 111. In this embodiment, the solid electrolyte layer 111 and the electrodes 112, 113 are collectively referred to as an Ip1 cell 110. The Ip1 cell 110 corresponds to a cell (specifically, a first pumping cell), and the electrodes 112, 113 correspond to a pair of electrodes in the present invention. More specifically, the electrodes 112, 113 correspond to a first counter electrode and an inside first pump electrode, respectively.

Next, the solid electrolyte layer 121 is disposed so as to face the solid electrolyte layer 111 via an insulator 140 which is sandwiched between the solid electrolyte layers 111, 121. Porous electrodes 122, 123 are disposed on both opposite surfaces of the solid electrolyte layer 121 so as to sandwich the solid electrolyte layer 121 therebetween. Similarly to the electrodes 112, 113, the porous electrodes 122, 123 are made of Pt or Pt alloy, cermet containing Pt and ceramic, or the like. The electrode 122 is formed on the surface of the solid electrolyte layer 121 which faces the solid electrolyte layer 111.

A hollow first measurement chamber 150 is defined between the solid electrolyte layer 111 and the solid electrolyte layer 121. Disposed on an inside of the first measurement chamber 150 are the electrode 113 on the side of the solid electrolyte layer 111 and the electrode 122 on the side of the solid electrolyte layer 121. The first measurement chamber 150 is a small space in the sensor element 100 into which the exhaust gas flowing through an exhaust passage is first introduced. A porous first diffusion resistance portion 151 is disposed on the front end side of the sensor element 100 in the first measurement chamber 150. The first diffusion resistance portion 151 serves as a partition separating the first measurement chamber 150 from the outside and restricts an amount of the exhaust gas flowing therethrough which is introduced into the first measurement chamber 150 per unit time. Similarly, a porous second diffusion resistance portion 152 is disposed on the rear end side of the sensor element 100. The second diffusion resistance portion 152 also serves as a partition separating the first measurement chamber 150 from an opening 141 opened to a second measurement chamber 160 as explained later and restricts an amount of the exhaust gas flowing therethrough which is introduced into the second measurement chamber 160 per unit time.

The solid electrolyte layer 121 and both electrodes 122, 123 associated therewith can generate electromotive force in accordance with s difference in oxygen partial pressure between the atmospheres separated by the solid electrolyte layer 121 (i.e., the atmosphere within the first measurement chamber 150 to which the electrode 122 is exposed, and the atmosphere within a reference oxygen chamber 170 to which the electrode 123 is exposed as explained later). In this embodiment, the structure constituted of the solid electrolyte layer 121 and both electrodes 122, 123 are collectively referred to as a Vs cell 120. The Vs cell 120 corresponds to a cell (specifically, an oxygen concentration detecting cell) in the present invention, and the electrodes 122, 123 correspond to a pair of electrodes in the present invention. More specifically, the electrodes 122, 123 correspond to a detecting electrode and a reference electrode, respectively, in the present invention.

Further, the Vs cell 120 of this embodiment also corresponds to an objective cell to be subjected to detection of an internal resistance thereof, in the present invention.

The solid electrolyte layer 131 is disposed in an opposed relation to the solid electrolyte layer 121 via the insulator 145 sandwiched therebetween. Disposed on the surface of the solid electrolyte layer 131 which faces the solid electrolyte layer 121 are porous electrodes 132, 133 made of Pt or Pt alloy, cermet containing Pt and ceramic, or the like. The electrodes 132, 133 correspond to a pair of electrodes in the present invention.

A reference oxygen chamber 170 as an independent space is formed in the position on the surface of the solid electrolyte layer 131 in which the insulator 145 is not present and the electrode 132 is disposed. The electrode 123 of the Vs cell 120 is disposed to be exposed to an inside of the reference oxygen chamber 170. The reference oxygen chamber 170 is filled with a porous ceramic member. Further, the insulator 145 is not present in a position on the surface of the solid electrolyte layer 131 in which the electrode 133 is disposed. The hollow second measurement chamber 160 is disposed in the position on the surface of the solid electrolyte layer 131 and defined as an independent small space by surrounding portions thereof. The second measurement chamber 160 is spaced apart from the reference oxygen chamber 170, between which the insulator 145 is disposed. Further, the solid electrolyte layer 121 and the insulator 140 have the openings 125 and 141, respectively, which are opened into the second measurement chamber 160 so that the solid electrolyte layer 121 and the insulator 140 are exposed to the second measurement chamber 160. As described above, the first measurement chamber 150 and the opening 141 are connected with each other via the second diffusion resistance portion 152 disposed therebetween.

Similarly to the Ip1 cell 110, the solid electrolyte layer 131 and both the electrodes 132, 133 can perform pumping-out of oxygen between the atmospheres separated by the insulator 145 (i.e., the atmosphere in the reference oxygen chamber 170 to which the electrode 132 is exposed, and the atmosphere in the second measurement chamber 160 to which the electrode 133 is exposed).

In this embodiment, the structure constituted of the solid electrolyte layer 131 and both the electrodes 132, 133 are collectively referred to as an Ip2 cell 130. The Ip2 cell 130 corresponds to a cell (specifically, a second pumping cell) in the present invention, and the electrodes 132, 133 correspond to a pair of electrodes in the present invention. More specifically, the electrodes 132, 133 correspond to a second counter electrode and an inside second pump electrode, respectively.

The electrode 113 of the Ip1 cell 110 on the side of the first measurement chamber 150, the electrode 122 of the Vs cell 120 on the side of the first measurement chamber 150, and the electrode 133 of the Ip2 cell 130 on the side of the second measurement chamber 160 are connected to a reference potential in the controller 1. One of the electrodes of the heater element 161 is grounded.

Next, the construction of the gas sensor control apparatus 1 electrically connected to the sensor element 100 is explained. The gas sensor control apparatus 1 includes a microcomputer 60, an electric circuit section 58, and the like. The microcomputer 60 includes a CPU 61, a RAM 62, a ROM 63, an A/D converter 65, a signal input/output section 64 which is communicated with the ECU 90 and connected with the CPU 61 and the A/D converter 65, a timer clock (not shown) and the like.

The electric circuit section 58 includes a reference voltage comparison circuit 51, an Ip1 drive circuit 52, a Vs detection circuit 53, an Icp supply circuit 54, an Ip2 detection circuit 55, a Vp2 apply circuit 56, a heater drive circuit 57 and a resistance detection circuit 59. The electric circuit section 58 detects concentration of NOx in the exhaust gas by using the NOx sensor 10 (the sensor element 100).

The Icp supply circuit 54 supplies a current Icp between the electrode 122 and the electrode 123 of the Vs cell 120 and performs pump-out of oxygen from the first measurement chamber 150 to the reference oxygen chamber 170. The Vs detection circuit 53 detects the voltage Vs between the electrodes 122, 123 of the Vs cell 120 and outputs the detection result to the reference voltage comparison circuit 51. The reference voltage comparison circuit 51 compares the voltage Vs between the electrodes 122, 123 detected by the Vs detection circuit 53 with a predetermined reference voltage (for instance, 425 mV) and outputs the comparison result to the Ip1 drive circuit 52.

The Ip1 drive circuit 52 supplies a current Ip1 between the electrode 112 and the electrode 113 of the Ip1 cell 110. On the basis of the result of comparison between the voltage Vs and the predetermined reference voltage by the reference voltage comparison circuit 51, the current Ip1 is adjusted in magnitude and direction such that the voltage between the electrodes 122, 123 of the Vs cell 120 is substantially equal to the predetermined reference voltage. Owing to the adjustment, pumping-out of oxygen from the first measurement chamber 150 to an outside of the sensor element 100 is carried out by the Ip1 cell 110, or pumping-in of oxygen from the outside of the sensor element 100 into the first measurement chamber 150 is carried out by the Ip1 cell 110. That is, the Ip1 cell 110 performs adjustment of oxygen concentration in the first measurement chamber 150 such that the voltage between the electrodes 122, 123 of the Vs cell 120 is kept at a constant value (i.e., a value of the predetermined reference voltage).

The Vp2 apply circuit 56 applies a constant voltage Vp2 (for instance, 450 mV) which acts to decompose the NOx (specifically, NO) in the gas to be measured (the exhaust gas) into oxygen and $N_2$, between the electrodes 132, 133 of the Ip2 cell 130. The Vp2 apply circuit 56 thus decomposes the NOx into nitrogen and oxygen and performs pumping-out of oxygen from the second measurement chamber 160 into the reference oxygen chamber 170 (i.e., from the electrode 133 to the electrode 132). The Ip2 detection circuit 55 detects a current Ip2 flowing between the electrodes 132, 133 of the Ip2 cell 130.

The heater drive circuit 57 is controlled by the CPU 61 and allows a current Vh to flow to the heater pattern 164 of the heater element 161 to thereby heat the solid electrolyte layers 111, 121, 131 (i.e., the Ip1 cell 110, the Vs cell 120, the Ip2 cell 130) and keep the temperature of the solid electrolyte layers 111, 121, 131 at a predetermined value (in other words, a target value). The heater pattern 164 is a single electrode pattern continuously extending in the heater element 161 and has one end grounded and the other end connected to the heater drive circuit 57.

The heater drive circuit 57 and the CPU 61 are configured to perform PWM control of the heater pattern 164 and control the current to be supplied to the heater pattern 164 on the basis of a value of an internal resistance of the Vs cell 120 as explained later, such that the solid electrolyte layers 111, 121, 131 (in this embodiment, specifically the solid electrolyte layer 121) have a target temperature. The heater drive circuit 57 and the CPU 61 correspond to a heater current supply control means according to the present invention.

Next, a method of measuring a value of the internal resistance (impedance) of the Vs cell 120 according to this embodiment is explained. The measurement of a value of the internal resistance of the Vs cell 120 is periodically carried out at a predetermined frequency. In the method of measuring a value of the internal resistance of the Vs cell 120, constant current I is supplied from a constant current source circuit which constitutes the resistance detection circuit 59, between the electrodes 122, 123 for a predetermined period of time, and the voltage V generated between the electrodes 122, 123 which changes in response to supply of the constant current I is measured by the resistance detection circuit 59. After that, the value of the internal resistance is calculated in the CPU 61 of the microcomputer 60 on the basis of the constant current I and a rate of change in the voltage V when the constant current I is supplied. More specifically, the voltage between the electrodes 122, 123 before the constant current I is supplied from the constant current source circuit provided in the resistance detection circuit 59 to the Vs cell 120, and the voltage between the electrodes 122, 123 when a predetermined period of time (for instance, 60 μs) has elapsed after the constant current I is supplied from the constant current source circuit to the Vs cell 120 are inputted via the resistance detection circuit 59 to the CPU 61. Then, the value of the internal resistance of the Vs cell 120 is calculated from a voltage difference (the rate of change in voltage) ΔV between the two voltages inputted by using a preset calculation formula or map. The construction of the resistance detection circuit 59 and the method of measuring the value of the internal resistance of the Vs cell 120 are conventionally known, and therefore, detailed explanations therefor are omitted. The resistance detection circuit 59 and the CPU 61 correspond to an internal resistance detection means according to the present invention.

Meanwhile, the measurement of the internal resistance value is not limited to that for the Vs cell 120, and internal resistance of the Ip1 cell 110 or the Ip2 cell 130 can be measured by the same manner as described above.

The thus constructed gas sensor control apparatus 1 performs an operation of detecting NOx concentration as follows.

With the temperature rise of the heater pattern 164 which is caused upon supply of a driving current by the heater drive circuit 57, the solid electrolyte layers 111, 121, 131 are heated and activated. As a result, the Ip1 cell 110, the Vs cell 120 and the Ip2 cell 130 are brought into an operable state.

On the other hand, the exhaust gas flowing through the exhaust passage (not shown) is introduced into the first measurement chamber 150 while being limited in amount by the first diffusion resistance portion 151. In this state, a slight amount of the current Icp is allowed to flow from the side of the electrode 123 of the Vs cell 120 toward the side of the electrode 122 of the Vs cell 120 by the Icp supply circuit 54. Therefore, the oxygen present in the exhaust gas can receive electrons from the electrode 122 in the first measurement chamber 150 which acts as a negative electrode, so that resulting oxygen ions flow through the solid electrolyte layer 121 into the reference oxygen chamber 170. That is, by flowing the current Icp between the electrode 122 and the electrode 123, the oxygen in the first measurement chamber 150 is fed to the reference oxygen chamber 170 in which the electrode 123 acts as the reference electrode.

The Vs detection circuit 53 detects the voltage between the electrodes 122 and 123. The voltage detected is compared with the reference voltage (425 mV) by the reference voltage comparison circuit 51. The comparison result is outputted to the Ip1 drive circuit 52. In this condition, if a concentration of the oxygen present in the exhaust gas introduced in the first measurement chamber 150 is adjusted such that a potential difference between the electrodes 122 and 123 is held at a substantially constant value of about 425 mV, the oxygen concentration in the exhaust gas in the first measurement chamber 150 can be approximated to a predetermined value (for instance, $10^{-8}$ to $10^{-9}$ atm).

Therefore, in a case where the oxygen concentration in the exhaust gas introduced into the first measurement chamber 150 is lower than the predetermined value, the Ip1 drive circuit 52 allows the current Ip1 to flow through the Ip1 cell 110 such that the electrode 112 acts as a negative electrode to perform pumping-in of oxygen from the outside of the sensor element 100 into the first measurement chamber 150. On the other hand, in a case where the oxygen concentration in the exhaust gas introduced into the first measurement chamber 150 is higher than the predetermined value, the Ip1 drive circuit 52 allows the current Ip1 to flow through the Ip1 cell 110 such that the electrode 113 acts as a negative electrode to perform pumping-out of oxygen from the first measurement chamber 150 to the outside of the sensor element 100.

The exhaust gas having the thus adjusted oxygen concentration in the first measurement chamber 150 is then introduced into the second measurement chamber 160 through the second diffusion resistance portion 152. The NOx present in the exhaust gas which is contacted with the electrode 133 in the second measurement chamber 160 is decomposed (reduced) into $N_2$ and $O_2$ by the electrode 133 as a catalyst. The oxygen thus obtained by the decomposition of NOx receives electrons from the electrode 133 and the resultant oxygen ions flow through the solid electrolyte layer 131 into the electrode 132. At this time, the residual oxygen which remains in the first measurement 150 without being pumped out and then introduced as such into the second measurement chamber 160 is subjected to pumping-in and allowed to move into the reference oxygen chamber 170 by the Ip2 cell 130. As a result, the current flowing in the Ip2 cell 130 seems to the current derived from the NOx and the current derived from the residual oxygen.

Since the concentration of the residual oxygen which remains in the first measurement 150 without being pumped out and then is introduced into the second measurement chamber 160 is adjusted to the predetermined value as described above, an amount of the current owing to the residual oxygen in the Ip2 cell 130 can be regarded as substantially constant so that the change in amount of the current owing to the residual oxygen has a less influence as compared to the change in amount of the current owing to the NOx. Therefore, the current flowing in the Ip2 cell 130 can be varied substantially in proportion to the NOx concentration. In the gas sensor control apparatus 1, a value of the current Ip2 flowing in the Ip2 cell 130 is detected by the Ip2 detection circuit 55, and the microcomputer 60 executes generally known processing for calculating correction of an offset current owing to the residual oxygen on the basis of the current value detected and performs detection of the NOx concentration in the exhaust gas.

The Ip2 detection circuit 55 and the microcomputer 60 correspond to a concentration value detection means according to the present invention.

Further, in the gas sensor control apparatus 1 according to this embodiment, in a case where the internal resistance value of the Vs cell 120 is varied to be out of a predetermined range due to element cooling or the like, it is determined that the detection value of the NOx concentration is incorrect and processing for outputting nullification information to nullify the detection value of the NOx concentration to the ECU 90 is executed.

Figure 2:
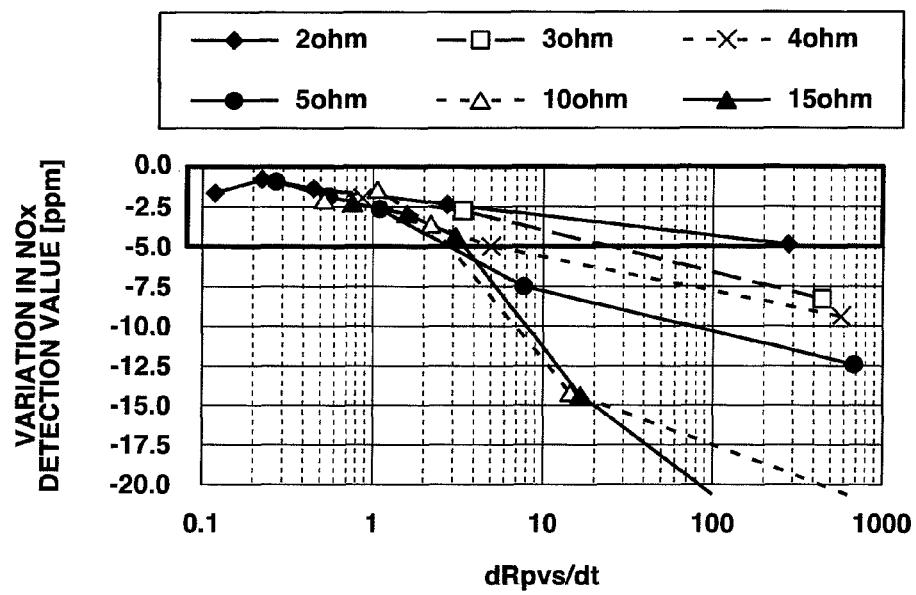
FIG. 2 is a graph showing a relationship between a rate of change in internal resistance value of a Vs cell of a NOx sensor with time (dRpvs/dt) and variation in detection value of NOx concentration.
Figure 3:
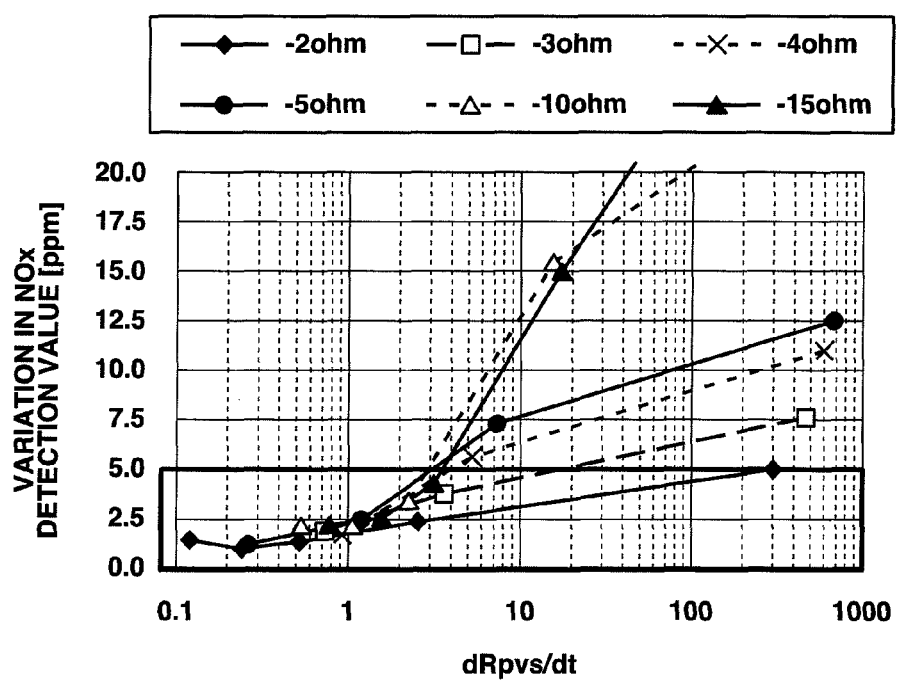
FIG. 3 is another graph showing a relationship between a rate of change in internal resistance value of a Vs cell of the NOx sensor with time (dRpvs/dt) and variation in detection value of the NOx concentration.
Figure 4:
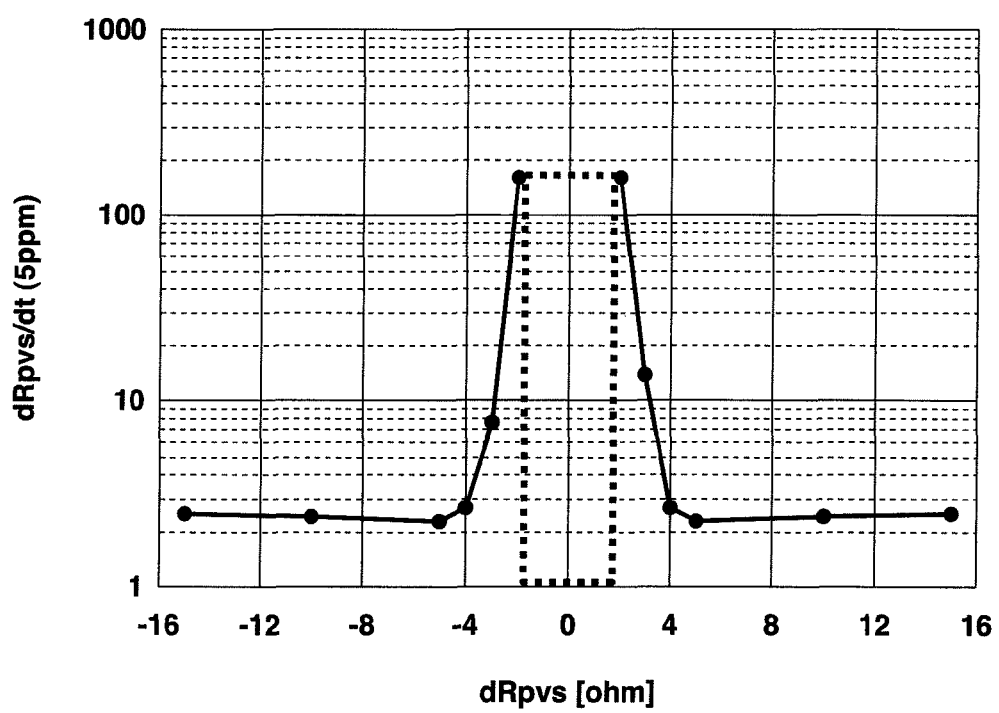
FIG. 4 is a graph showing a relationship between dRpvs and dRpvs/dt (5 ppm) in which a value of dRpvs/dt is determined from intersecting points at which respective dRpvs curves intersect with predetermined levels (±5 ppm) of variation in detection value of the NOx concentration (i.e., (dRpvs=±5 ppm).

Referring to FIG. 2 to FIG. 4, in advance of explaining the processing for outputting the nullification information to the ECU 90, the influence of element cooling or rapid temperature rise of element on the detection value of the NOx concentration in a case where variation in the internal resistance value of the Vs cell 120 as the objective cell is caused thereby is explained.

FIG. 2 is a graph showing a relationship between a rate of change (dRpvs/dt) in the internal resistance value of the Vs cell 120 with time and variation (ppm) in the detection value of the NOx concentration which is obtained under the following condition. That is, the NOx sensor 10 shown in FIG. 1 is disposed in an atmosphere (specifically, in atmospheric air) having a NOx concentration of 0 and a predetermined value of temperature, and the heater element 161 is controlled such that the internal resistance value of the Vs cell 120 becomes equal to the target value (300Ω). Assuming that element cooling occurs in this condition, the target value is intentionally changed by adding predetermined values to 300Ω (i.e., +2Ω, +3Ω, +4Ω, +5Ω, +10Ω, +1Ω as indicated in FIG. 2). Under the condition that the target value of the internal resistance for controlling the heater element 161 is thus changed, the variation (ppm) in the detection value of the NOx concentration with respect to the rate of change (dRpvs/dt) in the internal resistance value of the Vs cell 120 (hereinafter referred to as Rpvs as necessary) with time is plotted. For instance, in a case where the predetermined value intentionally added to the target value is +2Ω as shown in FIG. 2, a period of time t1 necessary for changing the target value from 300Ω to 302Ω is variously changed by variably controlling a current to be supplied to the heater element 161, and influence of the rate of change in Rpvs with time on the detection value of the NOx concentration is monitored. Accordingly, in this case, the rate of change (dRpvs/dt) is expressed as (302-300)/t1.

Further, FIG. 3 is a graph showing a relationship between a rate of change (dRpvs/dt) in the internal resistance value of the Vs cell 120 (hereinafter referred to as Rpvs as necessary) with time and variation (ppm) in the detection value of the NOx concentration which is obtained under the following condition. That is, the NOx sensor 10 shown in FIG. 1 is disposed in an atmosphere (specifically, in atmospheric air) having a NOx concentration of 0 and a predetermined value of temperature, and the heater element 161 is controlled such that the internal resistance value of the Vs cell 120 becomes equal to the target value (300Ω). Assuming that a rapid temperature rise of sensor element 100 occurs in this condition, the target value is intentionally changed by subtracting predetermined values from 300Ω (i.e., -2Ω, -3Ω, -4Ω, -5Ω, -10Ω, -15Ω as indicated in FIG. 3). Under a condition that the target value of the internal resistance for controlling the heater element 161 is thus changed, the variation (ppm) in the detection value of the NOx concentration with respect to the rate of change (dRpvs/dt) in the internal resistance value (hereinafter referred to as Rpvs as necessary) of the Vs cell 120 with For instance, as indicated by the characteristic curve obtained when the predetermined value intentionally added to the target value is +2Ω as shown in FIG. 2, as the value of dRpvs/dt becomes larger (that is, as the period of time necessary for changing Rpvs from 300Ω to 302Ω becomes shorter and thereby the sensor element temperature seems to be more rapidly dropped), the variation in the detection value of the NOx concentration is increased. The characteristic curves obtained when 3Ω, 4Ω, 5Ω, 10Ω and 15Ω are intentionally added to the target value, respectively, have a tendency almost similar to the characteristic curve obtained when 2Ω is intentionally added to the target value. However, the variation in the detection value of the NOx concentration as indicated by the characteristic curve obtained when 2Ω is intentionally added to the target value is smaller than those as indicated by the characteristic curves obtained when 3Ω, 4Ω, 5Ω, 10Ω and 15Ω are intentionally added to the target value, respectively. Accordingly, in a case where Rpvs is quickly changed with time, as dRpvs (i.e., change in the internal resistance value of the Vs cell 120 from 300Ω) becomes smaller, variation in the detection value of the NOx concentration can be reduced. Conversely, as dRpvs becomes larger, variation in the detection value of the NOx concentration is increased to thereby give an adverse influence on accuracy in detection of the NOx concentration. The above-described result is also shown in FIG. 3.

When variation in the detection value of the NOx concentration lies within the range of ±5 ppm, good accuracy in detection of the NOx concentration can be obtained. When this range is applied to vertical axes (variation in the detection value of the NOx concentration) of the graphs shown in FIG. 2 and FIG. 3, the range of ±5 ppm of variation in the detection value of the NOx concentration (accuracy in detection of the NOx concentration) is denoted by respective frames indicated by a thick solid line as shown in FIG. 2 and FIG. 3. In each of the frames of FIG. 2 and FIG. 3, an abscissa (dRpvs/dt) value at the intersecting point at which each of the characteristic curves of dRpvs (i.e., each of the plotted curves of +2Ω to +15Ω in FIG. 2 and each of the plotted curves of -2Ω to -15Ω in FIG. 3) intersects with the solid line of the frame (i.e., the solid line indicating -5 ppm or +5 ppm) of variation in the detection value of the NOx concentration is obtained. The value at the intersecting point is hereinafter referred to as dRpvs/dt (5 ppm). FIG. 4 shows a relationship between dRpvs and dRpvs/dt (5 ppm).

Meanwhile, FIG. 4 is prepared from a plurality of graphs corresponding to each of FIG. 2 and FIG. 3 by using a plurality of NOx sensors 10 (in this embodiment, three NOx sensors 10) in the following manner. That is, three graphs corresponding to FIG. 2 and three graphs corresponding to FIG. 3 are first prepared. In the respective three graphs, the value of dRpvs/dt at the intersecting point at which the characteristic curve of dRpvs intersects with the solid line indicating -5 ppm or +5 ppm of variation in the detection value of the NOx concentration is obtained for each dRpvs. An average value of the three values of dRpvs/dt thus obtained for each dRpvs is plotted on the graph as shown in FIG. 4.

As seen from FIG. 4, as the value of dRpvs becomes closer to 0 (in other words, the value of change in the internal resistance value of the Vs cell 120 from 300Ω becomes smaller), the value of dRpvs/dt (5 ppm) is increased. For instance, as shown in the graph obtained when 2Ω is intentionally added to the target value in FIG. 2, even when the value of dRpvs/dt becomes larger (about 300 of dRpvs/dt in FIG. 2), the value of variation in the detection value of the NOx concentration is still kept within the range of 5 ppm which is indicated by the thick solid line of the frame. This is because even if the value of Rpvs is rapidly changed, variation in the detection value of the NOx concentration is small (in other words, a good detection accuracy is readily kept), whereby an allowable amount of rapid change in the value of Rpvs (i.e., dRpvs/dt (5 ppm)) can be increased.

In contrast, as the value of dRpvs becomes larger, the value of dRpvs/dt (5 ppm) becomes smaller, whereby the allowable amount of rapid change in the value of Rpvs is reduced. In such a case, even when a slight change in the value of Rpvs with time occurs, the value of variation in the detection value of the NOx concentration will exceed 5 ppm. That is, as the value of dRpvs is smaller with respect to rapid change in the value of Rpvs which is caused due to element cooling or rapid temperature rise of element, variation in the detection value of the NOx concentration can be restricted within the predetermined range. However, in a general method of supplying a current to the heater 161, there seldom occurs a rapid change in the value of Rpvs which causes the value of dRpvs/dt (5 ppm) exceeding 100Ω/second. Therefore, 2Ω in which the value of dRpvs/dt (5 ppm) becomes not less than 100Ω/second is actually an upper limit value of dRpvs. For the above reason, in this embodiment, the upper limit value of dRpvs is set to not less than 2Ω. This value (i.e., 2Ω) corresponds to a permissible range of the target value of internal resistance according to the present invention.

Next, referring to FIG. 5 to FIG. 8, processing for nullifying the detection value of the NOx concentration which is executed by the gas sensor controlling apparatus 1 is explained.

Figure 5:
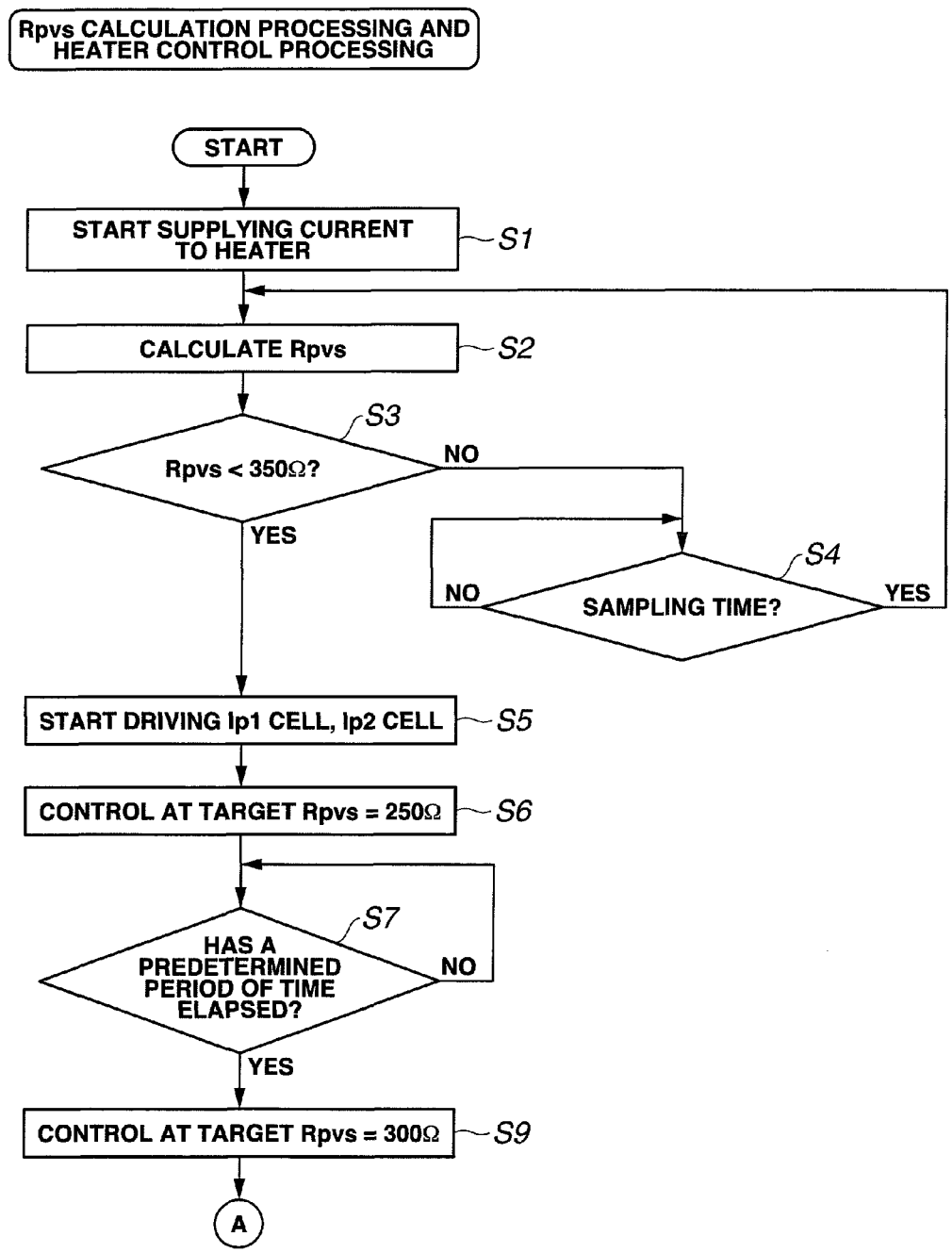
FIG. 5 is a flowchart illustrating a routine of processing for calculating a value of Rpvs and processing for controlling a heater.
Figure 6:
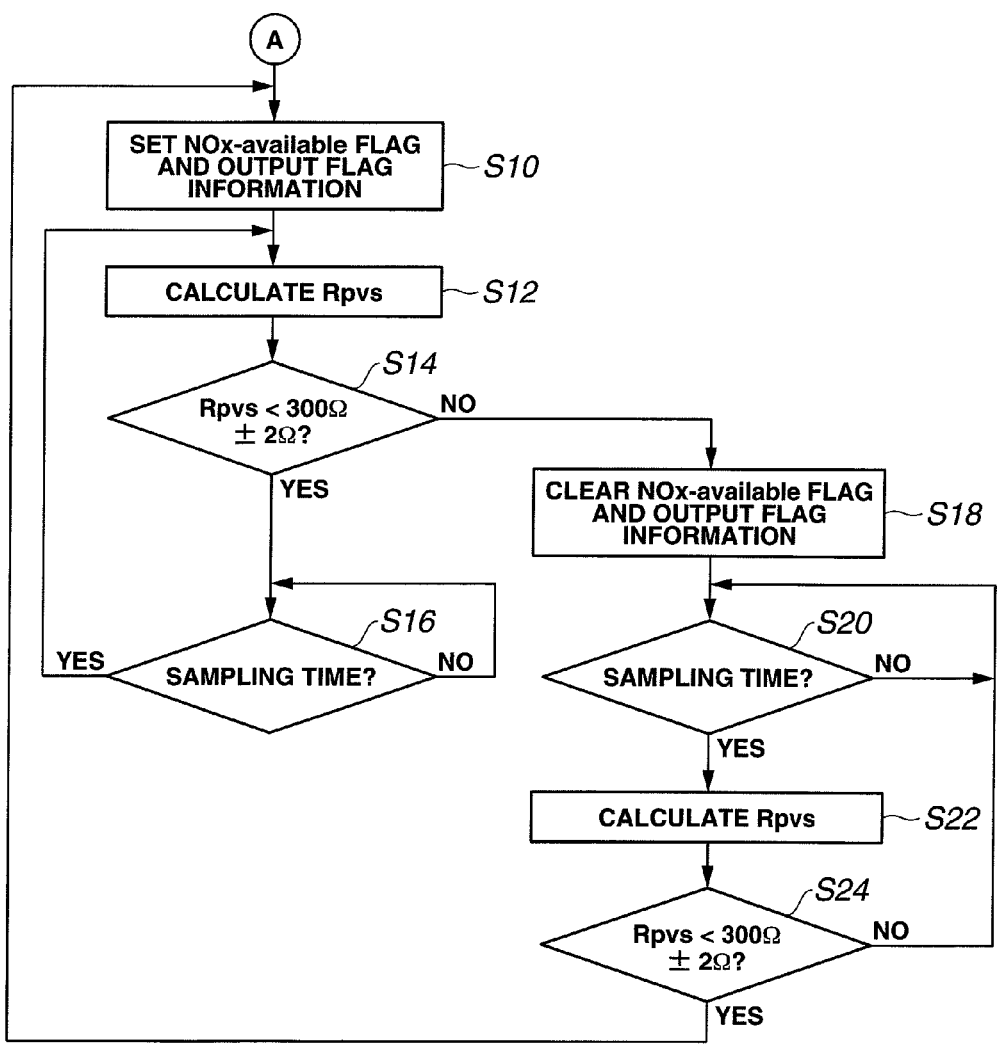
FIG. 6 is a flowchart illustrating a routine to be executed subsequent to the routine shown in FIG. 5.

FIG. 5 and FIG. 6 show a flow of processing for calculating a value of Rpvs and controlling the heater. As shown in FIG. 5, logic flow starts and goes to step S1. In step S1, in response to a sensor current supply start signal from the ECU 90 which is inputted to the CPU 61 via the signal input/output section 64, the CPU 61 controls the heater drive circuit 57 and starts supply of a current to the heater element 161 in response to the sensor current supply start signal inputted. Subsequently, in step S2, the CPU 61 calculates a value of internal resistance of the Vs cell 120 (Rpvs). In step S3, the CPU 61 determines whether or not the value of Rpvs is less than 350Ω. When the answer in the step S3 is YES, indicating that the value of Rpvs is less than 350Ω, the logic flow proceeds to step S5. In the step S5, the CPU 61 starts driving (controlling) the Ip1 cell 110 and the Ip2 cell 130. The logic flow then proceeds to step S6 in which the CPU 61 sets a target value of Rpvs to 250Ω and controls a current to be supplied to the heater element 161 (PWM control) by controlling the heater drive circuit 57. In the step S6, the CPU 61 also starts measurement of time.

On the other hand, when the answer in the step S3 is NO, indicating that the value of Rpvs is not less than 350Ω, the logic flow proceeds to step S4. In the step S4, the CPU 61 determines whether or not a sampling time has elapsed. When the answer in the step S4 is NO, the CPU 61 is on standby until the sampling time has elapsed. When the answer in the step S4 is YES, the logic flow goes back to the step S2.

In step S7, the CPU 61 determines whether or not a predetermined period of time (for instance, 30 seconds) has elapsed from the time at which the measurement of time is started in the step S6. When the answer in the step S7 is YES, indicating that the predetermined period of time has elapsed, the logic flow proceeds to step S9. In the step S9, the CPU 61 sets the target value of Rpvs to 300Ω and controls a current to be supplied to the heater element 161 (PWM control) by controlling the heater drive circuit 57. On the other hand, when the answer in the step S7 is NO, the CPU 61 is on standby until the predetermined period of time (sampling time) has elapsed.

Subsequent to the step S9, the CPU 61 continues execution of controlling supply of the current to the heater element 161 by setting the target value of Rpvs to 300Ω. Therefore, 300Ω corresponds to the target value of internal resistance Rpvs in the present invention.

Figure 7:
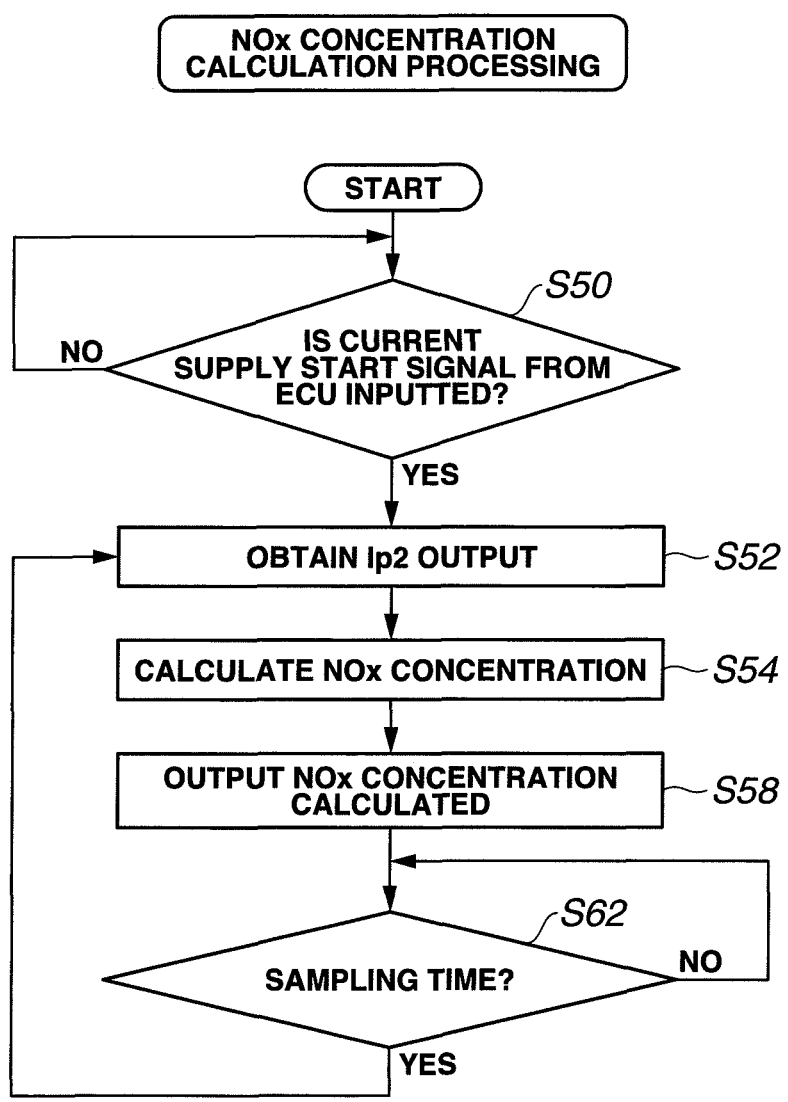
FIG. 7 is a flowchart illustrating a main routine of processing for calculating the NOx concentration.

After completion of the step S9, the logic flow proceeds to step S10 as shown in FIG. 6. In the step S10, the CPU 61 sets a NOx-available flag and outputs the flag information to the ECU 90 as the external device. Next, the logic flow proceeds to step S12 in which the CPU 61 calculates the value of Rpvs. The NOx-available flag is used for determination as to whether or not the NOx concentration value calculated in a main routine different from the routine shown in FIG. 5 and FIG. 6 (i.e., in the flow of processing as shown in FIG. 7) is to be nullified. The NOx-available flag corresponds to nullification information in the present invention. The CPU 61 corresponds to a nullification information generating means according to the present invention.

Subsequently, the logic flow proceeds to step S14 in which the CPU 61 determines whether or not the value of Rpvs is less than 300±2Ω (in other words, whether or not the value of Rpvs is larger than 298Ω and smaller than 302Ω). Here, 300Ω is the target value of internal resistance Rpvs as described above, and ±2Ω corresponds to a permissible range including the target value according to the present invention. Accordingly, the step S14 is the processing for determining whether or not the value of the internal resistance of the Vs cell 120 lies within the permissible range including the target value. In addition, the CPU 61 corresponds to a determination means according to the present invention.

When the answer in the step S14 is YES, the logic flow proceeds to step S16 in which the CPU 61 determines whether or not a sampling time has elapsed. When the answer in the step S16 is NO, the CPU 61 is on standby until the sampling time has elapsed. When the answer in the step S16 is YES, indicating that the sampling time has elapsed, the logic flow goes back to the step S12.

On the other hand, the answer in step S14 is NO, the logic flow proceeds to step S18 in which the CPU 61 clears the NOx-available flag and outputs the flag information to the ECU 90. The logic flow then proceeds to step S20 in which the CPU 61 determines whether or not a sampling time has elapsed. When the answer in the step S20 is NO, the CPU 61 is on standby until the sampling time has elapsed. When the answer in the step S20 is YES, indicating that the sampling time has elapsed, the logic flow proceeds to step S22. Meanwhile, the gas sensor control apparatus 1 according to this embodiment includes a CAN circuit (an interface with a network of the vehicle), not shown, which is connected to the ECU 90. The CAN circuit outputs (transmits) a High(1) signal indicative of the flag information concerning the NOx-available flag set in the step S10 to the ECU 90 upon setting the NOx-available flag, and outputs (transmits) a Low(0) signal indicative of the flag information concerning the NOx-available flag cleared in the step S18 to the ECU 90 upon clearing the NOx-available flag. The CPU 61 which gives the flag information concerning to the NOx-available flag to the ECU 90 corresponds to a nullification information output means according to the present invention.

Next, the logic flow proceeds to step S22 in which the CPU 61 calculates the value of Rpvs, and then proceeds to step S24 in which the CPU 61 determines whether or not the value of Rpvs is less than 300±2Ω. When the answer in the step S24 is YES, the logic flow goes back to the step S10. When the answer in the step S24 is NO, the logic flow goes back to the step S20.

Next, by referring to FIG. 7, a flow of the processing for calculating the NOx concentration as the main routine is explained.

As shown in FIG. 7, logic flow starts and goes to step S50 in which the CPU 61 determines whether or not the sensor current supply start signal from the ECU 90 is inputted to the CPU 61 via the signal input/output section 64. When the answer in the step S50 is YES, the logic flow proceeds to step S52 in which the CPU 61 obtains an Ip2 output. When the answer in the step S50 is NO, the logic flow goes back to the step S50. The Ip2 output is outputted to the CPU 61 in response to the start of driving the Ip2 cell at the step S5 as shown in FIG. 5. Subsequent to the step S52, the logic flow then proceeds to step S54 in which the CPU 61 calculates a value of NOx concentration on the basis of the Ip2 output. That is, the CPU 61 calculates the NOx concentration by detecting the Ip2 output (specifically, the current Ip2 flowing through the Ip2 cell 130).

Next, the logic flow proceeds to step S58 in which the CPU 61 outputs the calculated value of NOx concentration to the ECU 90 via the CAN circuit described above. The logic flow then proceeds to step S62 in which the CPU 61 determines whether or not the sampling time has elapsed. When the answer in the step S62 is NO, the CPU 61 is on standby until the sampling time has elapsed. When the answer in the step S62 is YES, the logic flow goes back to step S52.

Figure 8:
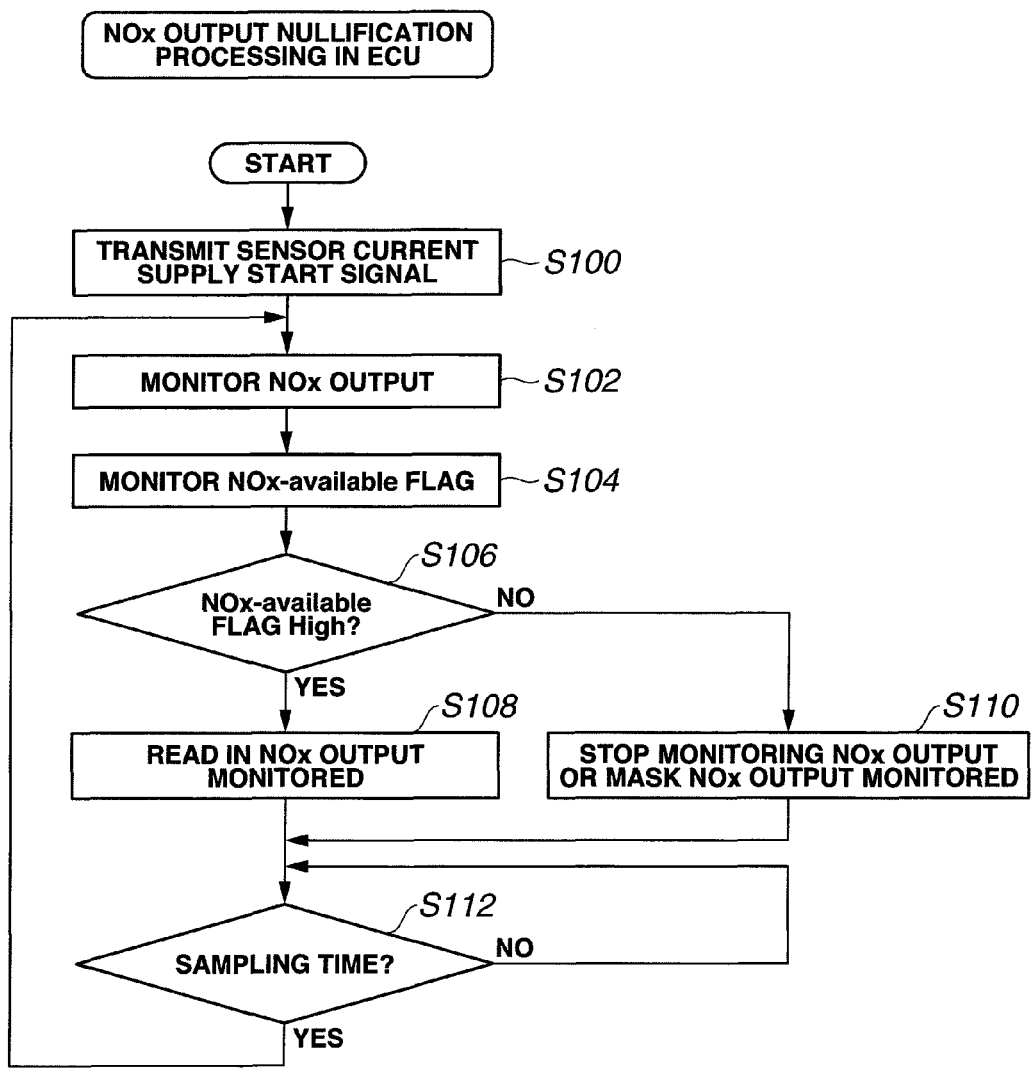
FIG. 8 is a flowchart illustrating a routine of processing for nullifying a NOx output in an ECU.

Referring to FIG. 8, a flow of processing for nullifying a NOx output in the ECU 90 is explained. In this embodiment, the nullification information (i.e., the flag information concerning to the NOx-available flag) as well as the NOx output (i.e., the calculated value of the NOx concentration) which are attained on the side of the gas sensor control apparatus 1 is transmitted to the ECU 90, and the determination as to whether or not the NOx output is to be nullified on the basis of the nullification information is made on the side of the ECU 90.

As shown in FIG. 8, logic flow starts and goes to step S100 in which the ECU 90 transmits the sensor current supply start signal to the CPU 60. The logic flow proceeds to step S102 in which the ECU 90 obtains (monitors) the output of the NOx concentration value (i.e., the calculated value of the NOx concentration), and then proceeds to step S104 in which the ECU 90 obtains (monitors) the flag information concerning to the NOx-available flag.

Subsequently, the logic flow proceeds to step S106 in which the ECU 90 determines whether or not the NOx-available flag is High (that is, the NOx-available flag is set). When the answer in the step S106 is YES, the logic flow proceeds to step S108. In the step S108, the ECU 90 reads-in the NOx output (the NOx concentration value) monitored in the step S102 as a final value and uses the NOx output for various controls. On the other hand, when the answer in the step S106 is NO, the logic flow proceeds to step S110 in which the ECU 90 stops monitoring the NOx output (the calculated NOx concentration value) or masks the monitored NOx output so as to prevent the monitored NOx output from being recognized as the final value.

If the ECU 90 stops the monitoring of the NOx output in the step S110, the ECU 90 cannot obtain the NOx concentration value during a period of time of stoppage. Specifically, when the target value of Rpvs (internal resistance of the Vs cell 120) with respect to rapid change in Rpvs which is caused due to element cooling or the like exceeds the permissible range ($\pm 2\Omega$), variation in NOx concentration value becomes excessively larger to thereby cause deterioration of accuracy in NOx concentration detection. For this reason, the NOx concentration value is prevented from being obtained during the period of time of stoppage, whereby deterioration of accuracy in NOx concentration detection can be suppressed. Similarly, deterioration of accuracy in NOx concentration detection can be suppressed by masking the monitored NOx output monitored during the period of time of masking. The masking method includes a method of converting the NOx output monitored during the period of time to a predetermined value (for instance, 0).

Subsequent to the step S108 and the step S110, the logic flow proceeds to step S112 in which the ECU 90 determines whether or not a sampling time has elapsed. When the answer in the step S112 is NO, the ECU 90 is on standby until the sampling time has elapsed. When the answer in the step S112 is YES, the logic flow goes back to step S102.

As explained above, in a case where the target value of the internal resistance of the Vs cell 120 with respect to rapid change in the value of Rpvs is out of the permissible range ($\pm 2\Omega$), the gas sensor apparatus 1 according to the present invention transmits the nullification information (the flag information indicating clearing of the NOx-available flag) to the ECU 90 independently of the NOx output. As a result, in a case where there occurs rapid change in the internal resistance Rpvs due to element cooling or the like, the ECU 90 does not recognize the detection value of the NOx concentration (the calculated NOx concentration value) as a final value on the basis of the flag information concerning to the NOx-available flag. Thus, the gas sensor apparatus 1 according to the present invention can suppress deterioration of accuracy in detection of the NOx concentration.

The gas sensor control method according to the present invention includes an internal resistance detection step (the step S2 in FIG. 5, the steps S12, S22 in FIG. 6), a concentration value detection step (the step S54 in FIG. 7), a heater current supply control step (the steps S6, S9 in FIG. 5), a determination step (the step S14 in FIG. 6), a nullification information generation step (the steps S10, S18 in FIG. 6) and a nullification information output step (the steps S10, S18 in FIG. 6).

Although the present invention has been described by reference to the above-described embodiment of the present invention, the present invention is not limited to the above-described embodiment.

For instance, the present invention is not limited to application to a NOx sensor and may be applied to an oxygen sensor, etc. Further, although the permissible range of internal resistance of the cell in the above embodiments is set to the same value ($2\Omega$) on both the "+" side and the "−" side with reference to the target value, the permissible range may be set to values different from each other between the "+" side and the "−" side with reference to the target value. Furthermore, the permissible range may be set to a value only on one of the "+" side and the "−" side and the target value as a lower limit value or an upper limit value on the other of the "+" side and the "−" side. Furthermore, when measuring a value of the internal resistance (impedance) of a cell (an objective cell), the internal resistance of the cell may be measured by using the volume of current variation which is obtained by supplying constant pulsed voltage to the cell.

This application is based on a prior Japanese Patent Application No. 2010-005606 filed on Jan. 14, 2010. The entire contents of the Japanese Patent Application No. 2010-005606 are hereby incorporated by reference.

Further variations of the embodiment and modification described above will occur to those skilled in the art in light of the above teachings. The scope of the invention is defined with reference to the following claims.

What is claimed is:

1. A method of controlling a gas sensor to suppress deterioration of accuracy caused due to temperature change, said gas sensor comprising a plurality of cells which each comprise a solid electrolyte layer and a pair of electrodes disposed on said solid electrolyte layer, and a heater adapted for heating at least one of said cells, said gas sensor being adapted for outputting a concentration signal corresponding to a concentration of a specific gas component present in a gas to be measured via one of said cells, said gas sensor being adapted for connecting to a gas sensor control apparatus which is connected with an external device, said method comprising:

an internal resistance detection step of detecting a value of an internal resistance of one of said cells as an objective cell;

a concentration value detection step of detecting a value of the concentration of said specific gas component on the basis of said concentration signal and outputting the value of the concentration to said external device;

a heater current supply control step of controlling a current to be supplied to said heater such that the value of the internal resistance detected in said internal resistance detection step becomes a target value;

a determination step of determining whether there is deterioration in accuracy in concentration detection by the concentration detection means, which is caused due to temperature change of said gas sensor, by determining whether or not the value of the internal resistance detected in said internal resistance detection step is within a permissible range including said target value;

a nullification information generation step of generating nullification information to nullify the value of the concentration which is detected in said concentration value detection step when it is determined in said determination step that the value of the internal resistance detected in said internal resistance detection step is out of said permissible range; and a nullification information output step of outputting said nullification information to said external device.

2. A gas sensor control apparatus adapted for connecting to an external device, said gas sensor control apparatus comprising:

a gas sensor comprising a plurality of cells which each comprise a solid electrolyte layer and a pair of electrodes disposed on said solid electrolyte layer, and a heater adapted for heating at least one of said cells, said gas sensor being adapted for outputting a concentration signal corresponding to a concentration of a specific gas component present in a gas to be measured via one of said cells, internal resistance detection means for detecting a value of an internal resistance of one of said cells as an objective cell;

concentration detection means for detecting a value of the concentration of said specific gas component on the basis of said concentration signal and outputting the value of the concentration;

heater current supply control means for controlling a current to be supplied to said heater such that the value of the internal resistance detected by said internal resistance detection means becomes a target value;

determination means configured to determine whether there is deterioration in accuracy in concentration detection by the concentration detection means, which is caused due to temperature change of said gas sensor, by determining whether or not the value of the internal resistance detected by said internal resistance detection means is within a permissible range including said target value;

nullification information generation means for generating nullification information to nullify the value of the concentration detected by said concentration detection means, when it is determined by said determination means that the value of the internal resistance detected by said internal resistance detection means is out of said permissible range; and nullification information output means for outputting said nullification information to said external device.

3. The gas sensor control apparatus as claimed in claim 2, wherein said gas sensor is a NOx sensor comprising a first measurement chamber defined between adjacent two of said solid electrolyte layers which are laminated spaced apart from each other, said gas to be measured being introduced from an outside into said first measurement chamber, and a second measurement chamber communicated with said first measurement chamber and defined by surrounding portions in the NOx sensor, said cells comprising:

an oxygen concentration measurement cell comprising a detection electrode disposed to be exposed to an inside of said first measurement chamber, and a reference electrode which is a counter electrode relative to the detection electrode, said oxygen concentration measurement cell outputting an output voltage corresponding to an oxygen concentration in said first measurement chamber, a first pumping cell comprising an inside first pump electrode disposed to be exposed to an inside of said first measurement chamber and a first counter electrode which is a counter electrode relative to said inside first pump electrode and disposed on an outside of said first measurement chamber, said first pumping cell controlling the oxygen concentration in said first measurement chamber by controlling a current flowing between said inside first pump electrode and said first counter electrode such that said output voltage from said oxygen concentration measurement cell becomes a predetermined value, and a second pumping cell comprising an inside second pump electrode disposed to be exposed to an inside of said second measurement chamber into which a gas whose oxygen concentration is controlled by said first pumping cell is introduced from said first measurement chamber, and a second counter electrode which is a counter electrode relative to said inside second pump electrode and disposed on an outside of said second measurement chamber, said second pumping cell through which a current corresponding to a concentration of NOx as said specific gas component present in the gas introduced into said second measurement chamber is flowed by applying a voltage between said inside second pump electrode and said second counter electrode, wherein one of said oxygen concentration measurement cell, said first pumping cell and said second pumping cell is the objective cell.

* * * * *